United States Patent
Hug et al.

(10) Patent No.: US 11,679,518 B2
(45) Date of Patent: Jun. 20, 2023

(54) MULTIFUNCTIONAL POCKET KNIFE

(71) Applicant: HELVETICA BRANDS SA, Delemont (CH)

(72) Inventors: Peter Hug, Nidau (CH); Arnaud Salin, Bermont (FR)

(73) Assignee: HELVETICA BRANDS SA, Delemont (CH)

(*) Notice: Subject to any disclaimer, the term of this patent is extended or adjusted under 35 U.S.C. 154(b) by 371 days.

(21) Appl. No.: 16/756,571

(22) PCT Filed: Oct. 16, 2018

(86) PCT No.: PCT/IB2018/001168
§ 371 (c)(1),
(2) Date: Apr. 16, 2020

(87) PCT Pub. No.: WO2019/077403
PCT Pub. Date: Apr. 25, 2019

(65) Prior Publication Data
US 2020/0238546 A1    Jul. 30, 2020

(30) Foreign Application Priority Data

Oct. 20, 2017  (CH) ..................... 01283/17

(51) Int. Cl.
*B26B 11/00*  (2006.01)
*A61B 17/50*  (2006.01)
(Continued)

(52) U.S. Cl.
CPC ............ *B26B 11/001* (2013.01); *A61B 17/50* (2013.01); *G02B 25/002* (2013.01); *A61B 2017/505* (2013.01); *B25F 1/04* (2013.01)

(58) Field of Classification Search
None
See application file for complete search history.

(56) References Cited

U.S. PATENT DOCUMENTS 5,116,347 A * 5/1992 Butler ............... A61B 17/50
606/205
5,246,449 A * 9/1993 Webster ............ A61B 17/50
606/1
(Continued)

FOREIGN PATENT DOCUMENTS

CA         2673153          1/2011
DE   202008003288 U1 *  7/2008 ........... A61B 17/50
(Continued)

OTHER PUBLICATIONS

International Search Report; International Application No. PCT/IB2018/001168; dated Dec. 6, 2019; 3 pages.
(Continued)

*Primary Examiner* — Monica S Carter
*Assistant Examiner* — Dana Lee Poon
(74) *Attorney, Agent, or Firm* — K&L Gates LLP

(57) ABSTRACT

The multifunctional pocket knife (1) is composed of a handle (2) formed by two joined-together flanks (3, 3') that provide at least one stowage space (4) for tools that each pivot about link pins (5, 5') arranged at each end of the handle (2). It is characterized in that it comprises a planar tick-removal instrument (6) that pivots about one of said link pins (5, 5') and that extends along the longitudinal axis of the pocket knife.
Tick-removal instrument (6) designed to be incorporated into a multifunctional pocket knife (1).

13 Claims, 4 Drawing Sheets

(51) Int. Cl.
*G02B 25/00* (2006.01)
*B25F 1/04* (2006.01)

(56) References Cited

U.S. PATENT DOCUMENTS

| | | | | |
|---|---|---|---|---|
| 5,400,451 | A  * | 3/1995 | Furukawa | B25F 1/04 |
| | | | | 7/106 |
| 5,447,511 | A  * | 9/1995 | Gadd | A61B 17/50 |
| | | | | 606/131 |
| 5,998,762 | A  * | 12/1999 | von der Heyde | A61B 17/50 |
| | | | | 219/229 |
| 10,980,572 | B1 * | 4/2021 | Poremba | A61B 17/50 |
| D940,321 | S  * | 1/2022 | Tatum | D24/147 |
| 2004/0003472 | A1* | 1/2004 | Dallas | B25F 1/003 |
| | | | | 7/128 |
| 2005/0081302 | A1* | 4/2005 | Elsener | B25F 1/04 |
| | | | | 7/118 |
| 2006/0271069 | A1* | 11/2006 | Glaesel | A61B 17/50 |
| | | | | 606/131 |
| 2008/0086822 | A1* | 4/2008 | Elsener | B26B 11/001 |
| | | | | 7/118 |
| 2011/0009881 | A1* | 1/2011 | Pabari | A61B 17/50 |
| | | | | 606/131 |
| 2016/0278811 | A1* | 9/2016 | Farnsworth | A01M 1/223 |
| 2019/0381647 | A1* | 12/2019 | Lazenby | B25F 1/003 |
| 2020/0189087 | A1* | 6/2020 | Henke | B26B 1/02 |

FOREIGN PATENT DOCUMENTS

| | | |
|---|---|---|
| DE | 20201703241 | 6/2017 |
| DE | 202017103241 | 6/2017 |

OTHER PUBLICATIONS

English Translation of International Search Report; International Application No. PCT/IB2018/001168; dated Dec. 6, 2019; 3 pages.
Written Opinion of International Searching Authority; International Application No. PCT/IB2018/001168; dated Dec. 6, 2019; 6 pages.

* cited by examiner

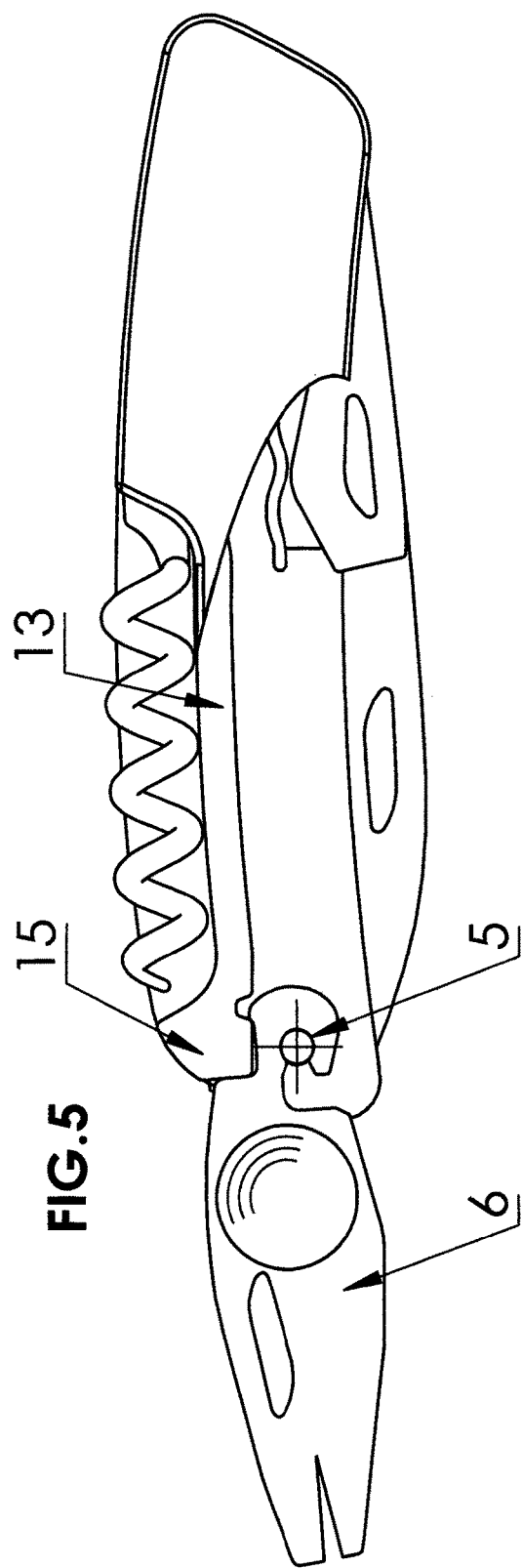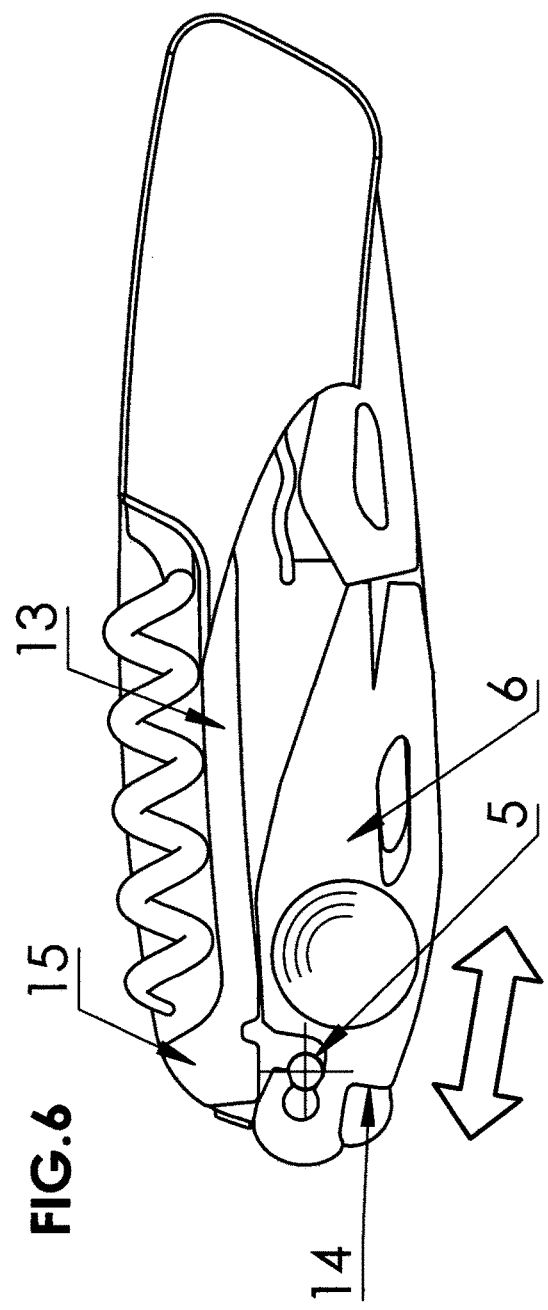

MULTIFUNCTIONAL POCKET KNIFE

PRIORITY CLAIMS

The present application is a National Stage of International Application No. PCT/IB2018/001168 filed on Oct. 16, 2018, which claims priority to Switzerland Patent Application No. 01283/17, filed Oct. 20, 2017, the entire contents of which are incorporated herein by reference.

INTRODUCTION

There is a wide variety of multifunctional pocket knives, the majority of which are characterized by the following arrangement: they are composed of a handle formed by two parallel flanks secured to one another by link pins and providing a stowage space designed to contain one or more tools or instruments, a knife blade, a screwdriver, an awl, a can opener, etc.

These tools or instruments are usually mounted such as to pivot about link pins, extending along the longitudinal axis of said pocket knife in such a manner as to extend said handle by means of the tool having the required function (cutting, sawing, screwing, etc.). Over the years, this type of pocket knife has become infinitely diversified and now incorporates ever more numerous and more complex tools or instruments.

In a completely different vein, when there is a need to remove a parasitic organism, such as a tick, from the skin of a human or an animal, the person skilled in the art has available a plurality of tick-removal variants such as, for example, those described in U.S. Pat. No. 5,246,449 or EP 0 821 571 B1. These are dedicated instruments that one does not necessarily take with one when out and about, in particular in areas likely to harbor such parasites, such as meadows, grassland, undergrowth or forests.

The issue has thus arisen of, insofar as is possible, combining such tick-removal instruments with an object that one frequently has on one's person when out and about, whether as hunter, shepherd, mushroom picker or simple walker, and in this case that object is a pocket knife.

Various combination or incorporation attempts have been explored, but to date without a satisfactory outcome, as the arrangement of a tick-remover requires technical adjustments that are incompatible with the particular features of a pocket knife. Currently, there is no assembly of this type in existence.

The present invention aims precisely to efficiently resolve the combining of a tick remover and a pocket knife.
The Invention The invention consists of a multifunctional pocket knife composed of a handle formed by two joined-together flanks providing at least one stowage space for tools that each pivot about link pins arranged at each end of the handle, characterized in that it comprises a flat tick-removal instrument that can move in rotation about one of said link pins and extends along the longitudinal axis of the pocket knife.

The invention likewise relates to a tick remover designed to be combined with or incorporated into a pocket knife and characterized in that it in a consists of planar element arranged such as to be mounted in rotation about one of the pins arranged at each of the ends of the handle of the knife, to extend along the longitudinal axis of said knife, and in that it comprises at its free end a cleft delimiting a "V"-shaped space expanding progressively toward said free end.

DRAWINGS

FIG. 5 illustrates the arrangement of the tick remover and of its return spring (open position).

FIG. 6 illustrates, opened-up, the tick remover in the functioning position immobilized by its return spring.

DEFINITIONS

The term "multifunctional" denotes a pocket knife that has commonplace tools or instruments, such as a knife blade, a screwdriver, a can opener, a punch, an awl, a corkscrew, for example, in addition to the aforementioned tick remover. Generally speaking, with a view to not overburdening the pocket knife or making it more complex beyond what is reasonable, one of the most underused tools in an existing model will be replaced by the tick remover of the invention.

The term "elastically deformable in bending" defines an optional variant of the tick remover, the embodiment of which will depend either on the configuration of the object, for example a plate that is very thin, particularly at its free end, or on the appropriate material of which it is composed, such as a polymer. The particular arrangement of one of these particular implementations of the invention will be described below.

The term "removable" also defines an optional variant of the invention. It aims to make it possible easily to replace the tick remover when the latter is worn, damaged or even broken. The particular arrangement of one of the particular implementations of the invention will be described below.

The term "gripping member" defines a tab such as is generally present on the various conventional tools or instruments of a pocket knife, knife blade, saw, screwdriver, etc., the particular feature of the invention consisting of a slot or other member traversing the body of the tick remover from one side to the other. The particular arrangement of one of the particular implementations of the invention will be described below.

PARTICULAR EMBODIMENTS OF THE INVENTION

Figure 1:
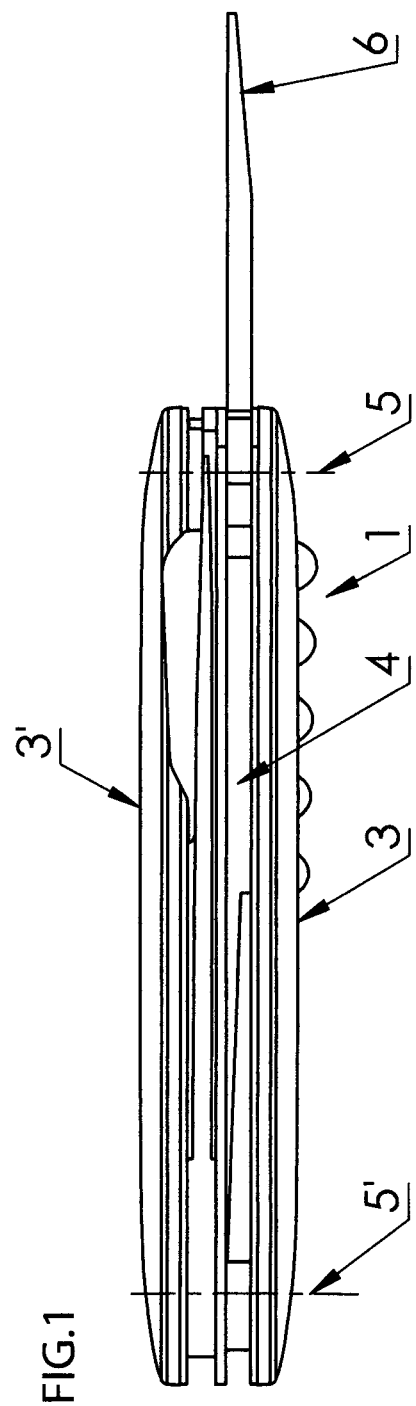
FIG. 1 illustrates, seen from above, the pocket knife and its tick remover in the functional state.
Figure 2:
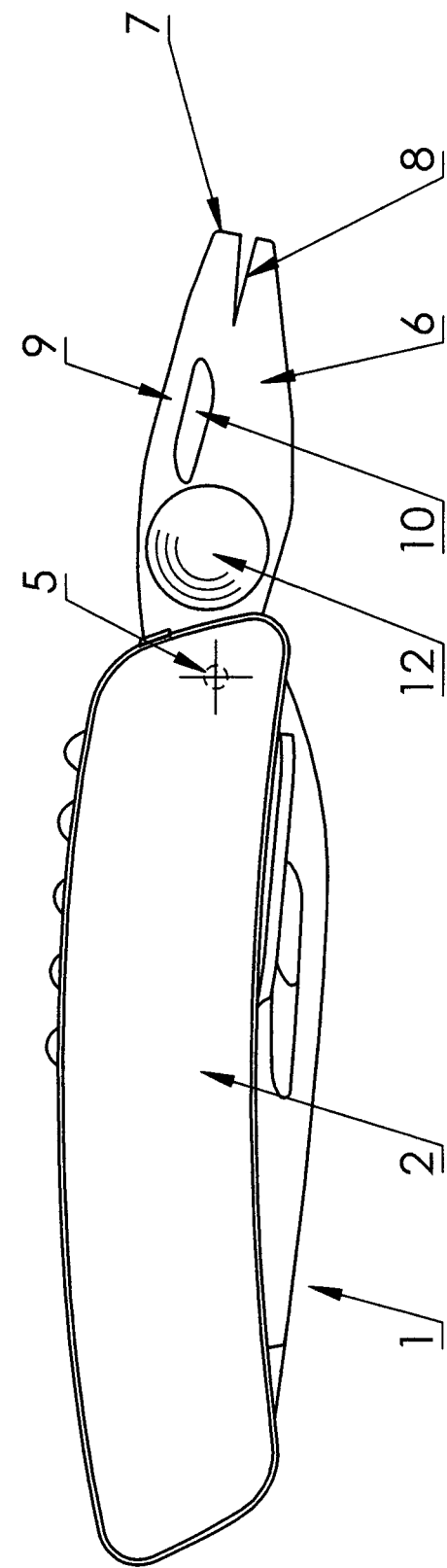
FIG. 2 is a profile view of the deployed tick remover according to FIG. 1.
Figure 3:
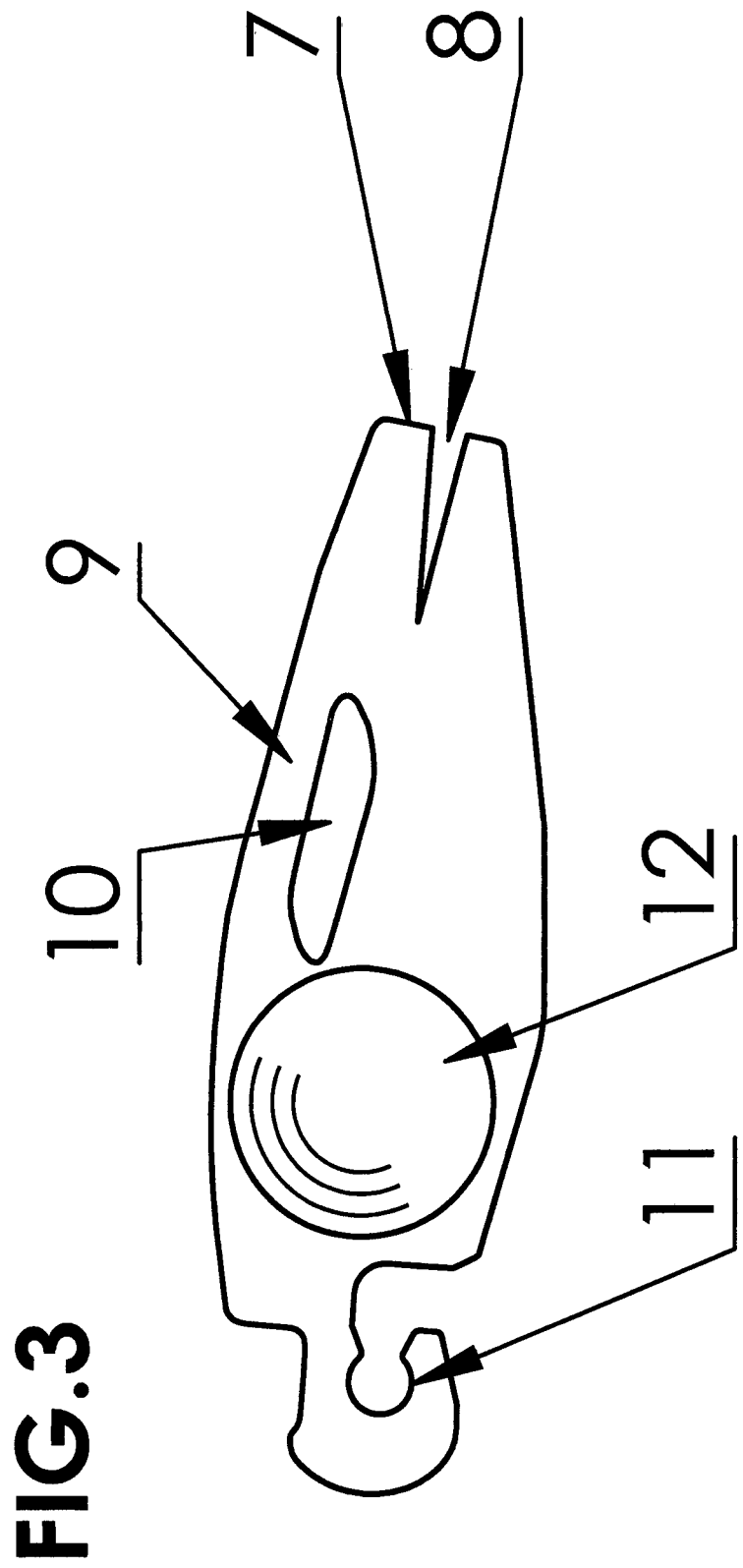
FIG. 3 is a profile view of a particular embodiment of the tick remover, detached from the pocket knife.

As illustrated in FIGS. 1 and 2, the pocket knife according to the invention is composed of a handle 2 formed by two joined-together flanks 3, 3' that provide at least one stowage space 4 for tools that each pivot about corresponding link pins 5, 5' arranged at each end of the handle 2.

Figure 4:
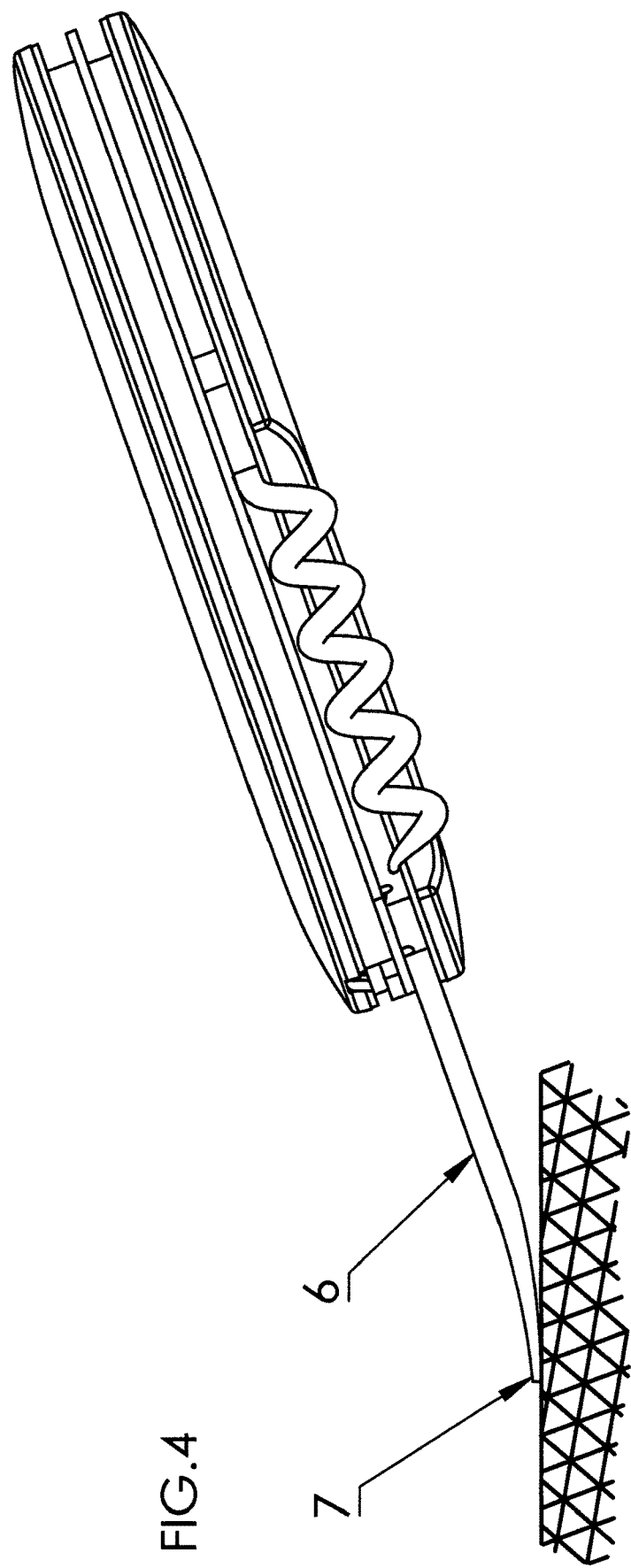
FIG. 4 is a lateral view showing the tick remover when bending.

The tick remover 6 is a planar instrument arranged such as to be movable in rotation about its pin 5 and to extend along the longitudinal axis of the pocket knife, just like a knife blade, for example. In a more particular embodiment, as illustrated in FIGS. 4 to 6, the tick remover 6 comprises, at one of its ends (called the rotary end), an open loop 11, the internal portion of which fits, in rotation, on the pin 5 and the external part (circumference) of which bears on the return spring 13.

Said external part is furthermore configured in such a manner that it provides a space or recess 14 that interacts, at the end of deployment of the tick remover 6, with the end or bulge 15 of said return spring 13, with a view to immobilizing the tick remover when it is deployed in order to be used.

The open look 11 has a cleft sufficient for it to be removed, by simple translational movement, from its rotation pin 5, through the effect of a longitudinal thrust or a longitudinal pulling action exerted, for example, from the free end 7 or from the gripping member 9 of the tick remover 6.

The pulling movement and the thrust exerted on the tick remover 6 are exerted along a slightly inclined axis relative to the general axis of the knife 1, this inclination being dependent ultimately on the configuration of the rotary end 11, and more precisely on the positioning of the aforementioned cleft. The axis of this type of movement in practice diverges by only a few degrees from the general axis of the knife. At the end of the pulling movement, moreover, said movement may be accompanied by a slight rotation.

The free or terminal end 7 of the tick remover 6 comprises a cleft 8 delimiting a "V"-shaped space that expands progressively toward said free end 7. This shape is ideal for the insertion of the tick remover 6 between the tick and the skin of the subject, because it adapts to the thickness of the detected parasite, which is more or less voluminous depending on the volume of blood it has sucked.

This particularly suitable configuration is furthermore promoted by the fact that the thickness of the tick remover 6 decreases from its rotary attachment point 11 to its free end 7 (see FIG. 1) and, optionally but not shown, by a trapezoidal cross section of said cleft 8 expanding from the bottom toward the top. This trapezoidal cross section may further vary in terms of width in such a manner as to adapt to the thickness of the detected parasite or to be provided with small teeth.

In a particular embodiment of the invention, the tick remover 6 is elastically deformable in bending relative to the plane of the tick remover. This bending, illustrated in FIG. 4, may depend equally on the configuration of the body of the tick remover 6 (see FIG. 1) or on the nature of the material of which it is composed, for example a sufficiently flexible metal or plastic blade. Deformation in bending, if desired, must be elastic such as to allow the reinsertion of the tick remover 6 in its housing 4 after it has been used.

There is, furthermore, a sizeable number of polymeric materials that may be machined (molded, stamped, cut, etc.) in order to yield a tick remover 6 that corresponds to the above features: polyvinyl chloride, polyacrylate, polyamide or the like, provided they have a suitable modulus of elasticity.

The polymeric material (monopolymer or copolymer) selected must likewise ensure sufficient elasticity for the cleft provided in the loop 11 to enlarge adequately upon forcible passage onto the pin 5 in the wake of the pulling movement or thrust exerted upon replacement of the tick remover 6, i.e. during its release from the stowage space 4 followed by its reinsertion into said stowage space (see FIG. 6).

In another particular embodiment of the invention, the tick remover 6 is provided with a gripping member 9, more particularly a slot 10 traversing the body of the tick remover from one side to the other: this configuration is most particularly favorable to the gripping of the instrument with a view to its deployment by either a right-handed or a left-handed person.

In another particular embodiment of the invention, the tick remover 6 comprises an optical instrument, such as a magnifier 12, inserted upstream of the "V"-shaped cleft. Said magnifier 12 may be inserted in the body of the tick remover 6 by any suitable means, as it is a separately manufactured, attached component. Three x magnification is generally sufficient and, moreover, compatible with the requirements of manufacturing techniques (see below).

When polymeric material is used (see above), a transparent or, otherwise, a sufficiently translucent polymer will be selected and the tick remover will be manufactured as a single component, for example by molding or melting/compression. With a view to facilitating the use thereof, that portion of the tick remover 6 that surrounds the magnifier 12 may be made opaque by means of an appropriate surface treatment (sand blasting, spraying with an opacifying agent, abrasion, etc.), said magnifier, however, remaining totally transparent.

Once the parasite, in this case the tick, has been detected on the skin surface, the user of the pocket knife of the invention grasps the handle 2 in one hand, seizes the gripping member 9 in the other and rotates the tick remover 6 out into its active position, secured by the embedding of the end 15 of the return spring 13 in the housing 14.

The user then brings the end 7 of the tick remover 6 close to the tick, where appropriate causing the body of the tick remover to bend (see FIG. 4), in such a manner as to cause the tick to penetrate as far as possible into the "V"-shaped cleft 8. When this has been completed, the tick is then removed from the skin by pulling vertically, where appropriate accompanied by slight or progressive twisting of the tick remover 6 about the vertical axis of the pulling movement. The magnifier 12 then makes it possible to check precisely whether there is any rostrum or rostrum debris remaining in the skin.

The deformation in bending mentioned above may in the long term lead to a structural weakening of the body of the tick remover 6, and this may likewise be the result of any impact on or dropping of the pocket knife with its tick remover deployed. The particular feature of the removable arrangement of the tick remover 6 according to one of the embodiments of the invention makes it possible advantageously to overcome this drawback.

The invention claimed is:
1. A multi-functional pocket knife comprising:
a handle formed by two integral flanks providing at least one storage space for tools each pivoting about connection axes arranged at each end of the handle, wherein the tools comprise a planar pulling tool movable in rotation about one of the connection axes and extending along a longitudinal axis of the pocket knife,
wherein the planar pulling tool is a tick remover which consists of a planar element comprising an opening at a free end of the tick remover, the opening delimiting a space gradually widening towards the free end,
the planar element comprising a gripping member adjacent to a slot passing through the planar element on either side, the planar element further comprising an optical instrument,
the planar element comprises a rotary end opposite from the free end, the planar element comprising an open loop at the rotary end, the open loop comprising an internal portion of the open loop which fits, in rotation, on a pin of the multifunctional pocket knife,
the open loop at the rotary end of the planar element comprises an external part which bears on a return spring of the multifunctional pocket knife, and the external part of the open loop comprises a recess configured to interact with the return spring to thereby immobilize the tick remover when the tick remover is deployed, and the open loop comprises a cleft configured for the open loop to be removed, by translational movement, from the pin.

2. The multifunctional pocket knife according to claim 1, wherein the free end of the tick remover is elastically deformable in flexion with respect to the plane of the tick remover.

3. The multifunctional pocket knife according to claim 1, wherein a thickness of the tick remover decreases from a rotary attachment point of the tick remover to the free end of the tick remover.

4. The multifunctional pocket knife according to claim 1, wherein the tick remover is movable in translation from an axis of rotation of the tick remover.

5. The multifunctional pocket knife according to claim 1 wherein the optical instrument comprises a magnifying glass.

6. The multifunctional pocket knife according to claim 5, wherein the magnifying glass is inserted upstream of the opening in the form of a V-shape.

7. A pull-out instrument for incorporation into a pocket knife, the pull-out instrument consisting of a planar element arranged to be mounted in rotation about an axis and extend along a longitudinal axis of the pocket knife, the planar element comprises an opening at a free end of the planar element, the opening delimiting a space gradually widening towards the free end, the planar element comprising a gripping member adjacent to a slot passing through the planar element on either side, the planar element further comprising an optical instrument, wherein the planar element is a tick remover comprising a rotary end opposite from the free end, the tick remover comprising an open loop at the rotary end, the open loop comprising an internal portion of the open loop which fits, in rotation, on a pin of the pocket knife, the open loop at the rotary end of the planar element comprises an external part which bears on a return spring of the pocket knife, and the external part of the open loop comprises a recess configured to interact with the return spring to thereby immobilize the tick remover when the tick remover is deployed, and the open loop comprises a cleft configured for the open loop to be removed, by translational movement, from the pin.

8. The pull-out instrument according to claim 7, wherein the free end of the planar element is elastically deformable in bending with respect to the plane of the planar element.

9. The pull-out instrument according to claim 7, wherein a thickness of the planar element decreases from a rotary attachment point of the planar element to the free end.

10. The pull-out instrument according to claim 7, wherein the planar element is arranged to be removably mounted in translation from an axis of rotation of the planar element.

11. The pull-out instrument according to claim 7, wherein the planar element is made of a polymer material.

12. The pull-out instrument according to claim 7, wherein the optical instrument comprises a magnifying glass.

13. The pull-out instrument according to claim 12, wherein the magnifying glass is inserted upstream of the opening in the form of a V-shape.

* * * * *